United States Patent
Kim et al.

(10) Patent No.: US 11,471,224 B2
(45) Date of Patent: Oct. 18, 2022

(54) ENDOSCOPE ROBOT

(71) Applicant: KOREA INSTITUTE OF SCIENCE AND TECHNOLOGY, Seoul (KR)

(72) Inventors: Keri Kim, Seoul (KR); Geunwoong Ryu, Seoul (KR); Chulmin Park, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 1017 days.

(21) Appl. No.: 16/181,353

(22) Filed: Nov. 6, 2018

(65) Prior Publication Data

US 2019/0388163 A1    Dec. 26, 2019

(30) Foreign Application Priority Data

Jun. 26, 2018   (KR) .................. 10-2018-0073251

(51) Int. Cl.
    *A61B 34/30*      (2016.01)
    *A61B 1/005*      (2006.01)
    (Continued)

(52) U.S. Cl.
    CPC ............ *A61B 34/30* (2016.02); *A61B 1/0008* (2013.01); *A61B 1/008* (2013.01); *A61B 1/0016* (2013.01);
    (Continued)

(58) Field of Classification Search
    CPC ........... A61B 2017/00477; A61B 2017/00318; A61B 2017/00305; A61B 34/71;
    (Continued)

(56) References Cited

U.S. PATENT DOCUMENTS 6,409,672 B2 *  6/2002  Webler ............... G01S 7/52079
                                                      600/463
9,526,582 B2   12/2016  Kim et al.
                        (Continued)

FOREIGN PATENT DOCUMENTS

JP          06319697 A     11/1994
JP       2000227559 A      8/2000
                (Continued)

OTHER PUBLICATIONS

S.M. Kim et al. "Development of a Finger-like Mechanism of End-Effector for Micro Surgery,", IEEE Engineering in Medicine and Biology Society, 2016, pp. 5224-5227.

*Primary Examiner* — Vi X Nguyen
(74) *Attorney, Agent, or Firm* — Cantor Colburn LLP (57) ABSTRACT

Endoscope apparatus includes: a tube unit coupled to a rotary shaft to which a rotational force is transmitted so as to be rotatable, the tube unit being formed to extend in one direction; steering unit having one end installed at one end of the tube unit to rotate with respect to the tube unit so that a direction thereof facing forward is adjusted, the steering unit rotating together with the tube unit by the rotational force transmitted from the tube unit; an end effector installed inside the steering unit to rotate together with the steering unit due to the rotation of the steering unit, the end effector being disposed to face forward; and shaft-fixing tube body installed at the end effector, wherein the direction of the steering unit facing forward and relative rotation of the steering unit with respect to the end effector are adjustable.

7 Claims, 7 Drawing Sheets

(51) Int. Cl.
*A61B 1/00* (2006.01)
*A61B 1/233* (2006.01)
*A61B 1/05* (2006.01)
*A61B 1/008* (2006.01)
*A61B 34/00* (2016.01)
*A61M 25/01* (2006.01)
*A61B 17/00* (2006.01)

(52) U.S. Cl.
CPC .......... *A61B 1/0051* (2013.01); *A61B 1/0055* (2013.01); *A61B 1/0057* (2013.01); *A61B 1/00137* (2013.01); *A61B 1/00183* (2013.01); *A61B 1/05* (2013.01); *A61B 1/233* (2013.01); *A61B 34/71* (2016.02); *A61B 2017/00305* (2013.01); *A61B 2017/00318* (2013.01); *A61B 2017/00477* (2013.01); *A61B 2034/301* (2016.02); *A61B 2034/715* (2016.02); *A61M 25/0116* (2013.01); *A61M 2025/015* (2013.01)

(58) Field of Classification Search
CPC ..... A61B 34/30; A61B 19/201; A61B 19/203; A61B 19/5244; A61B 1/00; A61B 1/005; A61B 1/233; A61B 1/0057; A61B 1/0016; A61M 2025/015
See application file for complete search history.

(56) References Cited

U.S. PATENT DOCUMENTS

| | | | |
|---|---|---|---|
| 2007/0102473 A1* | 5/2007 | Shelton | A61B 17/07207 227/175.1 |
| 2007/0158385 A1* | 7/2007 | Hueil | A61B 17/07207 227/175.1 |
| 2014/0309625 A1* | 10/2014 | Okamoto | A61B 34/71 606/1 |
| 2015/0032117 A1 | 1/2015 | Kim et al. | |
| 2016/0192823 A1 | 7/2016 | Yasunaga et al. | |

FOREIGN PATENT DOCUMENTS

| | | |
|---|---|---|
| JP | 5861017 B1 | 2/2016 |
| KR | 1020150014156 A | 2/2015 |
| KR | 101525457 B1 | 6/2015 |

* cited by examiner

ENDOSCOPE ROBOT

CROSS-REFERENCE TO RELATED APPLICATION

This application claims priority to Korean Patent Application No. 10-2018-0073251, filed on 26 Jun. 2018, and all the benefits accruing therefrom under 35 U.S.C. § 119, the contents of which in its entirety are herein incorporated by reference.

BACKGROUND

1. Field

The present disclosure relates to an endoscope robot, and more particularly, to an endoscope robot capable of adjusting a location of an endoscope terminal.

2. Description of the Related Art

Brain base surgery (Endonasal Skull Base Surgery) is being conducted to observe and remove brain tumors such as meningioma in the intracranial core, especially on the brain base.

In order for a surgical instrument to access the brain base, a surgical instrument having a fine thickness, which may be inserted through the nasal cavity, is generally used.

In an existing system, a driving shaft adjusts an image sensor in a vertical direction or in a lateral direction to obtain an image. For this, an endoscope should be driven by giving an x-axis or y-axis input by means of inverse kinematics. Also, the existing system has a problem of a large volume.

In this case, the existing system has a problem in that the image rotates, and a separate software correction operation such as cutting out a rectangular image sensor into a circular shape is required. Meanwhile, the existing system is not able to perform stereoscopic imaging.

SUMMARY

The present disclosure is directed to providing an endoscope robot, which may easily control a direction while advantageously securing a work area due to its small operating volume.

In one aspect, there is provided an endoscope apparatus, comprising: a tube unit coupled to a rotary shaft to which a rotational force is transmitted so as to be rotatable, the tube unit being formed to extend in one direction; a steering unit having one end installed at one end of the tube unit to rotate with respect to the tube unit so that a direction thereof facing forward is adjusted, the steering unit rotating together with the tube unit by the rotational force transmitted from the tube unit; an end effector installed inside the steering unit to rotate together with the steering unit due to the rotation of the steering unit, the end effector being disposed to face forward; and a shaft-fixing tube body installed at the end effector, wherein the direction of the steering unit facing forward and a relative rotation of the steering unit with respect to the end effector are adjustable.

According to an embodiment of the present disclosure, a steering protrusion may be protrusively formed on an outer circumference at one end of the steering unit, and a steering hole accommodating the steering protrusion may be formed at one end of the tube unit.

Preferably, a guide protrusion may be protrusively formed on an outer circumference of the end effector so that the end effector is guided to rotate by the rotation of the steering unit, and a rotation guide may be formed at the steering unit along a rotation direction of the steering unit to accommodate the guide protrusion.

According to another embodiment of the present disclosure, a connection member may be installed between the end effector and the shaft-fixing tube body to connect the end effector and the shaft-fixing tube body, the connection member may include a first protrusion protruding to connect the end effector relatively rotatably and a second protrusion protruding to connect the shaft-fixing tube body relatively rotatably, a hole may be formed in the end effector so that the first protrusion is rotatably inserted therein, and a hole may be formed in the shaft-fixing tube body so that the second protrusion is rotatably inserted therein.

Preferably, a wire hole may be formed in the steering unit so that a wire is installed therein, the wire hole may be formed at both sides with the steering protrusion being interposed therebetween, and the direction of the steering unit facing forward may be adjusted by changing a tension of the wires respectively installed in the wire holes.

Preferably, a steering cut portion may be formed at an outer circumference of the tube unit adjacent to the steering hole to have a space in which the steering unit is rotatable.

According to still another embodiment of the present disclosure, a rotation cut portion may be formed at an outer circumference of the shaft-fixing tube body adjacent to the hole into which the second protrusion is rotatably inserted, to have a space in which the end effector is rotatable.

According to still another embodiment of the present disclosure, the endoscope apparatus of the present disclosure may further comprise a steering driving unit configured to generate a driving force and transmit the generated driving force to the steering unit so that the steering unit is rotatable with respect to the tube unit, and the steering driving unit may include: a steering driving motor connected to a power source to generate a rotation driving force by receiving a power therefrom; a driving gear connected to the steering driving motor to receive a rotation driving force generated by the steering driving motor and transmit a driving force to enable the wire to be wound or unwound; and a wire connected to the driving gear and installed at the wire hole of the steering unit.

According to still another embodiment of the present disclosure, the endoscope apparatus of the present disclosure may further comprise a rotation driving unit configured to generate a driving force and transmit the generated driving force to the shaft-fixing tube body so that the steering unit is rotatable with respect to the end effector, the rotation driving unit may include a rotation driving motor connected a power source to generate a rotation driving force by receiving a power therefrom, the tube unit may be connected to the rotation driving motor to rotate by receiving the rotation driving force generated by the rotation driving motor, and the tube unit may allow the rotational force to be transmitted to the steering unit.

DETAILED DESCRIPTION

Hereinafter, the embodiments disclosed in this specification will be described in detail. Here, identical or similar components are denoted by identical or similar reference symbols and not described in detail again. In the following description, the word "unit" used in terms is selected or endowed only in consideration of ease naming and does not have any distinguishable meaning or role. In addition, in the following description of the embodiments of the present disclosure, any detailed description of related arts can be omitted if it is determined that the gist of the embodiments disclosed herein can be obscured by the same. Moreover, it should be understood that the accompanying drawings are just for better understanding of the embodiments disclosed herein and are not to be construed as limiting the scope of the present disclosure. The scope of the present disclosure should be understood as including all changes, equivalents and alternatives thereof.

Terms having an ordinal such as "first" and "second" can be used for explaining various components, but the components are not limited by the terms. These terms are just used for distinguishing any component from another.

In case it is mentioned that any component is "connected" to another component, the component may be connected directly to another component, but it should be understood that any other component can be further interposed between them.

The singular expressions are intended to include the plural forms as well, unless the context clearly indicates otherwise.

In this specification, the term such as "include" and "have" is just to specify the presence of features, integers, steps, operations, elements, parts or components thereof, stated in the specification, but does not preclude the presence or addition of one or more other features, integers, steps, operations, elements, parts or components thereof.

Figure 1:
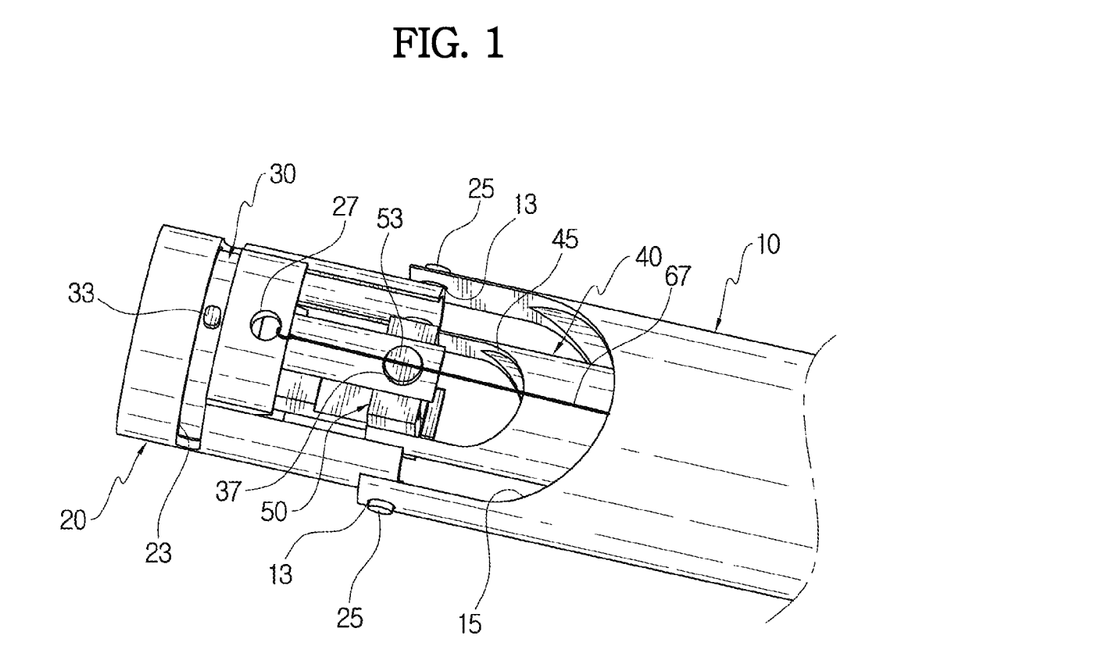
FIG. 1 is a perspective view showing an end of an endoscope apparatus according to the present disclosure in an enlarged state.
Figure 2A:
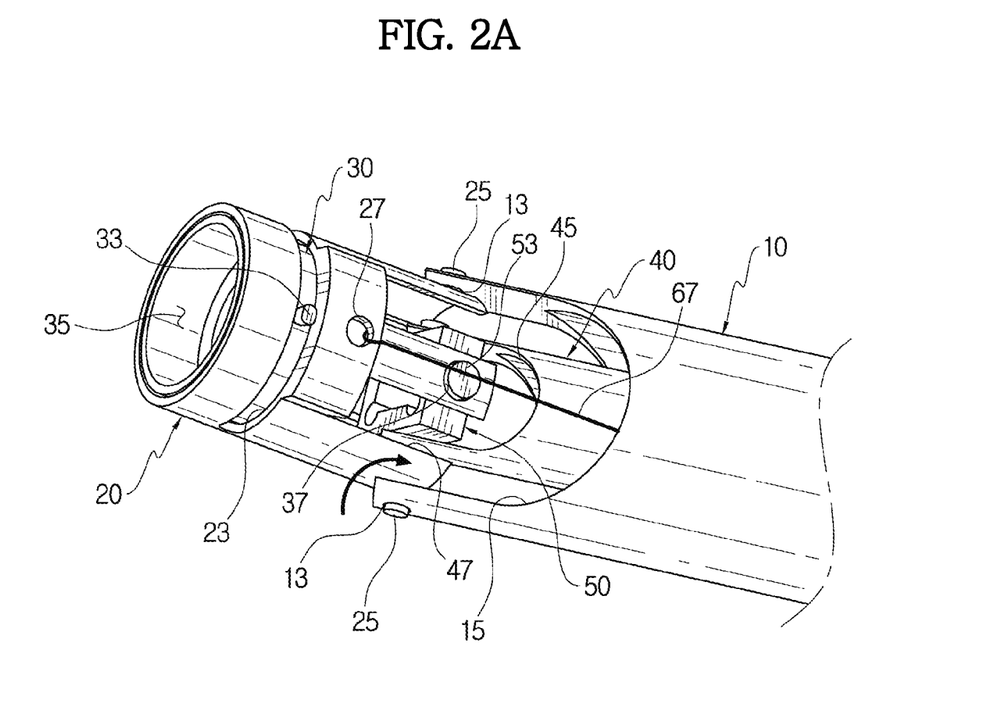
FIG. 2A is a diagram showing an operation state where a steering unit is rotated to one side with reference to a tube unit as an example.
Figure 2B:
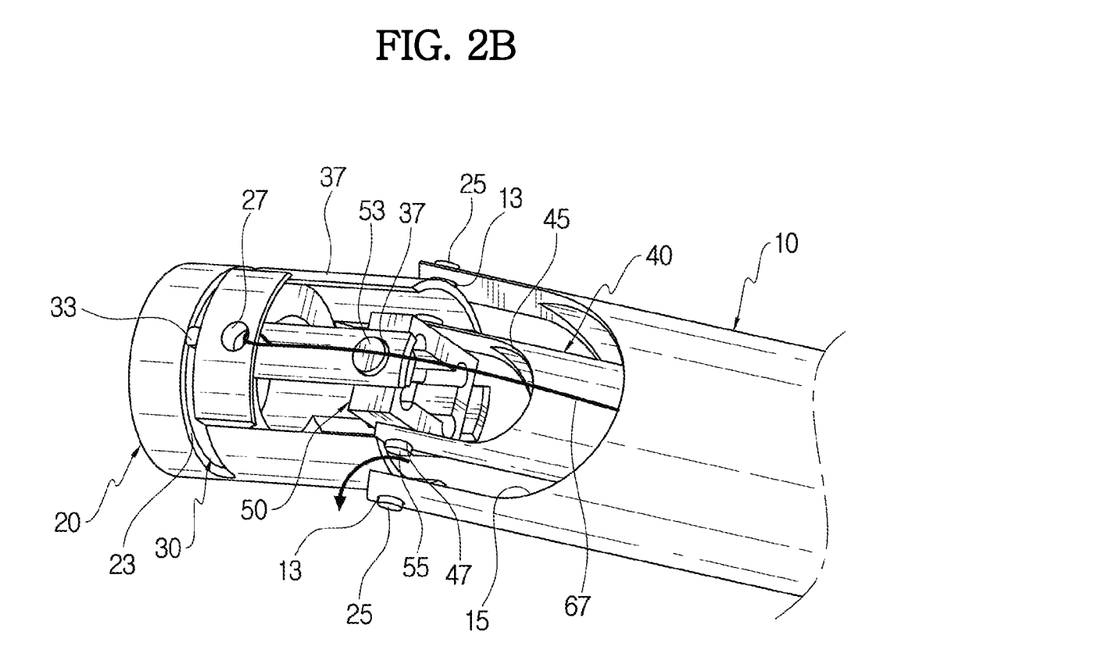
FIG. 2B is a diagram showing an operation state where the steering unit is rotated to another side with reference to the tube unit as an example.
Figure 3A:
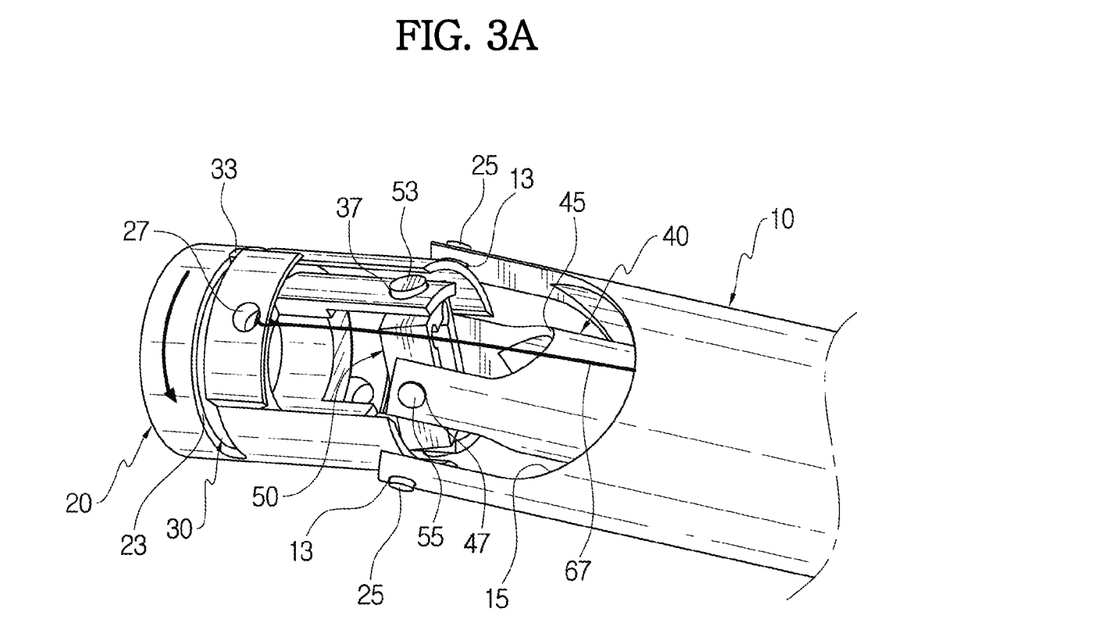
FIG. 3A is a diagram showing an operation state where the steering unit is rotated to another side with reference to the tube unit and the steering unit is rotated to one side with reference to an end effector as an example.
Figure 3B:
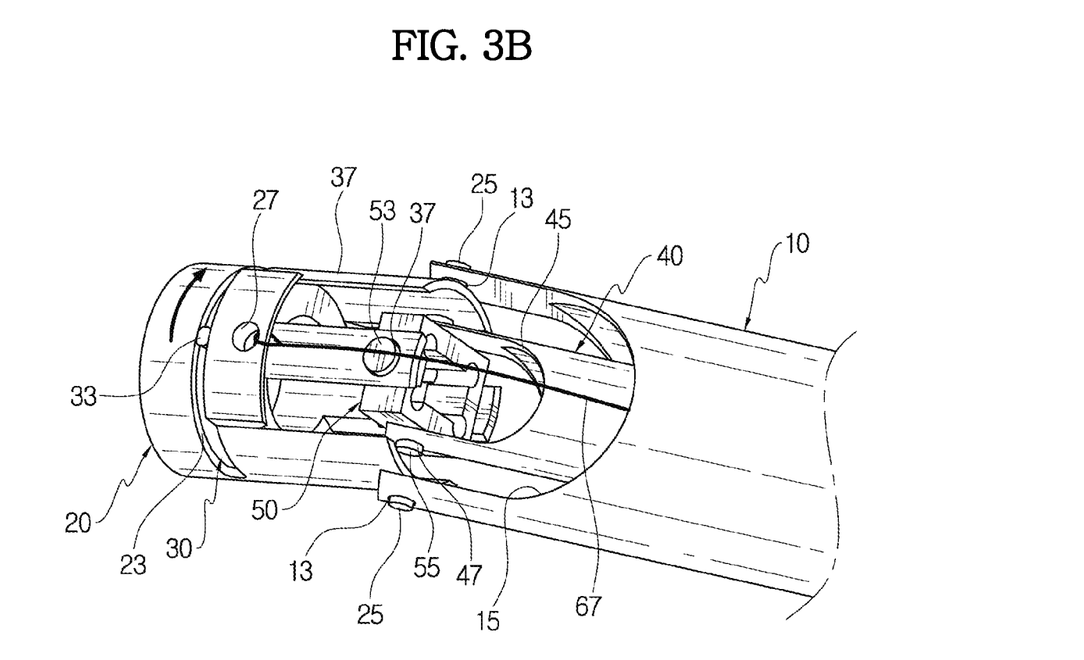
FIG. 3B is a diagram showing an operation state where the steering unit is rotated to another side with reference to the tube unit and the steering unit is disposed at one point between one side and another side of the end effector as an example.
Figure 3C:
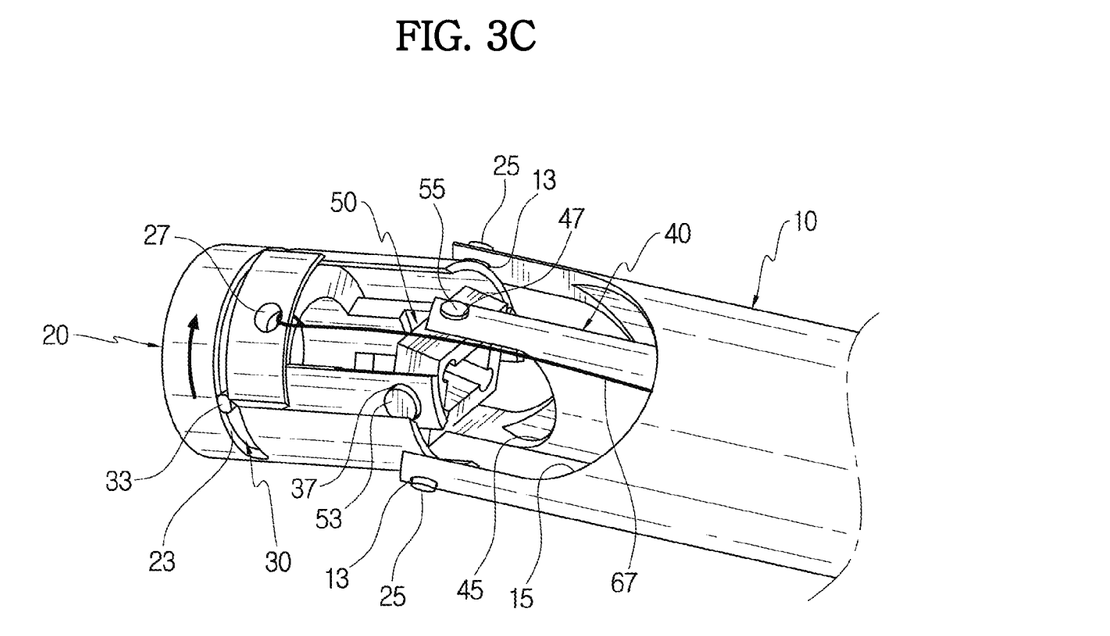
FIG. 3C is a diagram showing an operation state where the steering unit is rotated to another side with reference to the tube unit and the steering unit is rotated to another side with reference to the end effector.

FIG. 1 is a perspective view showing an end of an endoscope apparatus 100 according to the present disclosure in an enlarged state, FIG. 2A is a diagram showing an operation state where a steering unit 20 is rotated to one side with reference to a tube unit 10 as an example, FIG. 2B is a diagram showing an operation state where the steering unit 20 is rotated to another side with reference to the tube unit 10 as an example, FIG. 3A is a diagram showing an operation state where the steering unit 20 is rotated to another side with reference to the tube unit 10 and the steering unit 20 is rotated to one side with reference to an end effector as an example, FIG. 3B is a diagram showing an operation state where the steering unit 20 is rotated to another side with reference to the tube unit 10 and the steering unit 20 is disposed at one point between one side and another side of the end effector as an example, and FIG. 3C is a diagram showing an operation state where the steering unit 20 is rotated to another side with reference to the tube unit 10 and the steering unit 20 is rotated to another side with reference to the end effector.

Referring to FIGS. 1 to 3C, the structure and operation of the endoscope apparatus 100 according to the present disclosure will be described.

The endoscope apparatus 100 of the present disclosure includes a tube unit 10, a steering unit 20, an end effector 30 and a shaft-fixing tube body 40.

Figure 4:
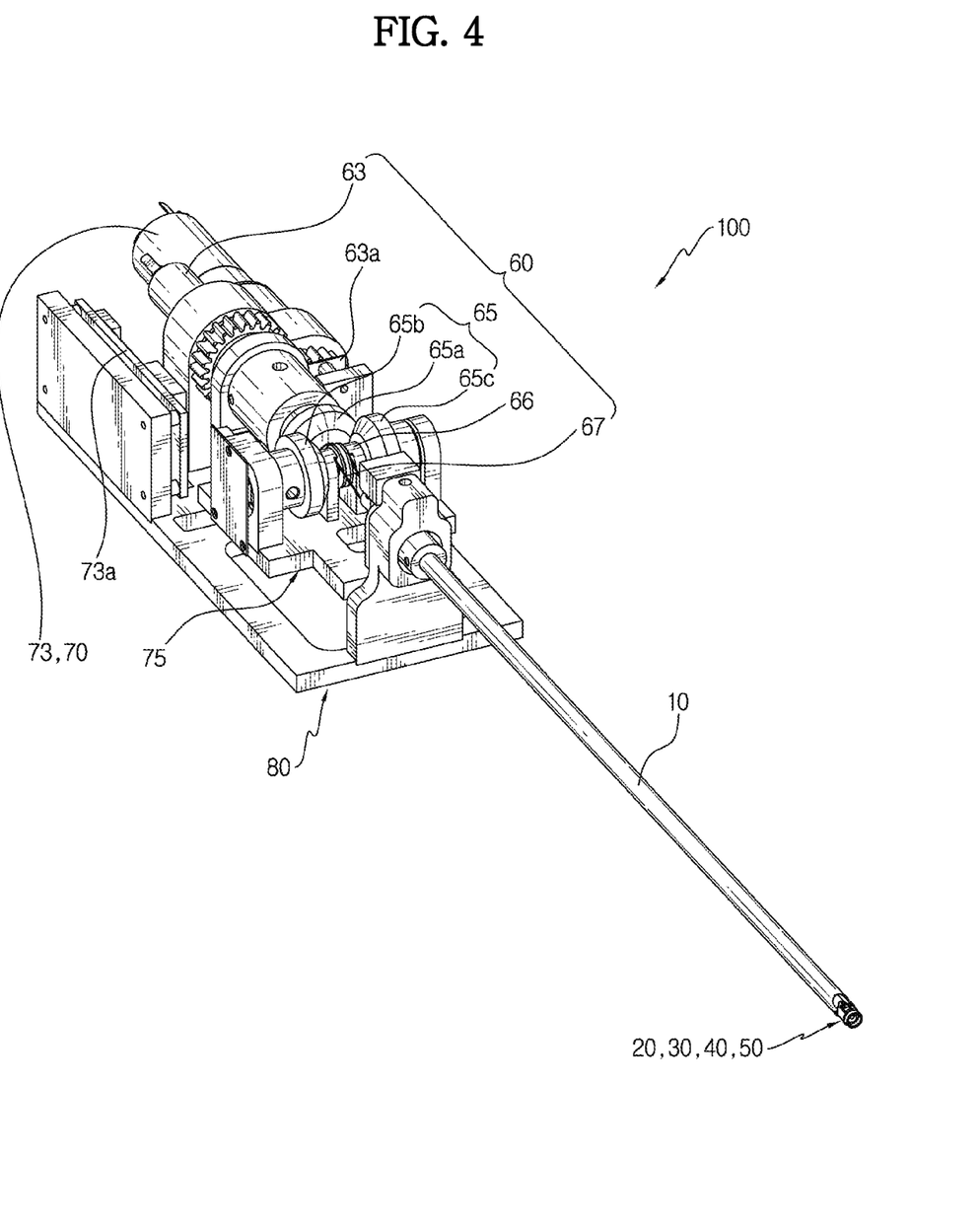
FIG. 4 is a perspective view showing the endoscope apparatus according to the present disclosure.

The tube unit 10 extends in one direction to have a predetermined length (see FIG. 4). The tube unit 10 has an accommodation portion in which components such as a rotary shaft and a shaft-fixing tube body 40, explained later, may be accommodated. A steering hole 13 may be formed at one end of the tube unit 10, and the steering unit 20, explained later, may be rotatably installed at the steering hole 13. In addition, the tube unit 10 is coupled to a rotary shaft (not shown) to which a rotational force is transmitted, to provide a rotational force to the steering unit 20.

One end of the steering unit 20 is installed at one end of the tube unit 10 so that a direction facing forward is adjusted. For example, the steering unit 20 is connected to the tube unit 10 to rotate together with the tube unit 10, and it may be understood that the steering unit 20 rotates so that a first central axis extending from the center of the steering unit 20 and a second central axis extending from the center of the tube unit 10 intersect each other. In addition, the steering unit 20 rotates together with the tube unit 10 by the rotational force transmitted from the tube unit 10. That is, the steering unit 20 rotates coaxially with the tube unit 10 and rotates so that the direction facing forward is adjustable such that its central axes intersect each other with respect to the tube unit 10.

Referring to FIGS. 2A and 2B, based on a state where the steering unit 20 and the tube unit 10 are arranged to be parallel to each other, the steering unit 20 may rotate about 135° in both directions depicted by arrows in FIGS. 2A and 2B, respectively. That is, the steering unit 20 is installed at the end of the tube unit 10 so as to be rotatable about 270° in total.

For example, a steering protrusion 25 may be formed on an outer circumference at one end of the steering unit 20, and a steering hole 13 may be formed at one end of the tube unit 10 to accommodate the steering protrusion 25 to be rotatable. By doing so, the steering unit 20 may rotate relative to the tube unit 10 about the steering protrusion 25.

In addition, as shown in FIGS. 1 to 2B and the like, a steering cut portion 15 is formed at an outer circumference of the tube unit 10 to have a space for allowing the steering unit 20 to rotate. The steering cut portion 15 is preferably formed adjacent to the steering hole 13 of the tube unit 10.

Meanwhile, the steering unit 20 may have a wire hole 27 in which a wire 67 may be installed. The wire hole 27 is preferably formed at a suitable position at which the steering unit 20 is rotatable about the steering protrusion 25 due to the tension of the wire 67. Even though FIG. 1 shows an example in which the wire hole 27 is formed in one side of the steering unit 20, the wire hole 27 is preferably formed in one side of the steering unit 20 as shown in FIG. 1 and in another side opposite thereto, which is not shown in the figure. Accordingly, the wires 67 are provided in the wire holes 27 at both sides, respectively, and the direction of the steering unit 20 facing forward is adjusted by changing the tension applied to each wire 67.

The end effector 30 is disposed to face forward. In addition, the end effector 30 is installed inside the steering unit 20 and is guided by the rotation of the steering unit 20 to be rotatable together with the steering unit 20. For example, the end effector 30 may be installed inside the steering unit 20 such that the central axis of the end effector 30 is rotated in parallel with the central axis of the steering unit 20. A sensor accommodation portion 35 (shown in FIG. 2A) at which an image sensor for obtaining an image of the periphery of a surgical site is installed may be provided at one end of the end effector 30 facing forward.

However, the component installed to the sensor accommodation portion 35 at one end of the end effector 30 facing forward is not limited to the image sensor, and it should be understood that any micro working device capable of performing various operations in a tube may be installed thereto. For example, at one end of the end effector 30, a working device capable of photographing, incising, cutting, penetrating, sealing, bonding (welding) or lighting a workpiece, or applying or administrating a medicine may be installed.

If the endoscope robot is used for a minimally invasive procedure, a small surgical device such as a camera, a surgical scalpel, scissors, a syringe or a laser device may correspond thereto. In this case, the tube unit 10 may serve as a passage through which a substance such as a drug may flow and be supplied to the end effector 30.

A guide protrusion 33 may be formed at an outer circumference of the end effector 30 to protrude so that the end effector 30 is guided by rotation of the steering unit 20 to rotate. In addition, the steering unit 20 may have a rotation guide 23 formed along the rotation direction of the steering unit 20 to accommodate the guide protrusion 33. FIGS. 1 to 3B show an example in which the rotation guide 23 is depicted in a sectioned form as much as 180° along the outer circumference of the steering unit 20 in the rotation direction of a fixed socket.

A shaft-fixing tube body 40 is installed at the end effector 30. The shaft-fixing tube body 40 is accommodated in the tube unit, and if the end effector rotates together with the steering unit due to the rotation of the steering unit, the shaft-fixing tube body 40 is rotated together.

In this structure, the endoscope apparatus 100 of the present disclosure may adjust the direction of the front steering unit 20 facing forward and a relative rotation of the steering unit 20 with respect to the end effector 30. For example, the shaft-fixing tube body 40 may be disposed in the accommodation portion of the tube unit 10.

Also, a connection member 50 may be installed between the end effector 30 and the shaft-fixing tube body 40 to connect the end effector 30 and the shaft-fixing tube body 40.

The connection member 50 may include a first protrusion 53 protruding to connect the end effector 30 relatively rotatably, and a second protrusion 55 protruding to connect the shaft-fixing tube body 40 relatively rotatably. The first and second protrusions 53, 55 may protrude in directions intersecting each other at the outer circumference of the connection member 50.

The end effector 30 has a hole 37 formed so that the first protrusion 53 is rotatably inserted therein, and the shaft-fixing tube body 40 may have a hole 47 formed so that the second protrusion 55 is rotatably inserted therein.

Meanwhile, a rotation cut portion 45 may be formed at the outer circumference of the shaft-fixing tube body 40, and the rotation cut portion 45 has a space for allowing the end effector 30 to be rotatable. An example in which the rotation cut portion 45 is disposed adjacent to the hole 47 at the outer circumference of the shaft-fixing tube body 40 is shown in FIG. 1 or the like.

Due to this structure, as shown in FIGS. 3A to 3C, even when the steering unit 20 is rotated with respect to the tube unit 10 by a predetermined angle, the steering unit 20 may rotate with respect to the end effector 30 without damaging the end effector 30 and the shaft-fixing tube body 40. In addition, in a state in which the steering unit 20 is rotated at a predetermined angle with respect to the end effector 30, the steering unit 20 may rotate smoothly with respect to the tube unit 10.

Hereinafter, components for transmitting a driving force to the steering unit 20, the shaft-fixing tube body 40 and the end effector 30, explained before, will be described with reference to FIG. 4.

The endoscope apparatus 100 of the present disclosure may further include a steering driving unit 60 and a rotation driving unit 70.

The steering driving unit 60 generates a driving force and transmits the generated driving force to the steering unit 20 so that the steering unit 20 may rotate relative to the tube unit 10.

The steering driving unit 60 may include a steering driving motor 63, a driving gear 65 and a wire 67.

The steering driving motor 63 is connected to a power source (not shown) to receive a power and generate a rotation driving force. Also, a sensing board 63a for controlling the rotation of the steering unit 20 by adjusting the tension applied to the wire 67 may be electrically connected to the steering driving motor 63.

The driving gear 65 receives the rotational driving force generated by the steering driving motor 63 and transmits a power to enable the wire 67 to be wound or unwound.

The driving gear 65 includes, for example, a first bevel gear 65a connected to the steering driving motor 63 to rotate, and second and third bevel gears 65b, 65c arranged to intersect the first bevel gear 65a and configured to receive the power from the first bevel gear 65a.

Referring to FIG. 4, the second and third bevel gears 65b, 65c are disposed at 90° with respect to the first bevel gear 65a. Also, a wire fixture 66 is installed at an end of each of the second and third bevel gears 65b, 65c, and the wire 67 is wound on the wire fixture 66. The structure of the driving gear 65 is not limited to the structure shown in FIG. 4, but may have various mechanical mechanisms capable of transmitting the rotation driving force generated by the steering driving motor 63 to allow the wire 67 to be wound or unwound.

One end of the wire 67 is wound on the wire fixture 66, and the wire 67 is wound or unwound by the driving force transmitted from the steering driving motor 63. In addition, the other end of the wire 67 is installed at the wire hole 27 of the steering unit 20, explained above, to allow the steering unit 20 to rotate in a wound or unwound state. Two wires 67 may be provided so as to be installed at two wire holes 27, explained above, respectively. In this case, since the sensing board 63a, explained above, adjusts the tension of the two wires 67, the steering unit 20 may be rotated due to a difference in tension transmitted to the wires 67.

Meanwhile, the wire 67 may be disposed inside the shaft-fixing tube body 40 as an example.

The rotation driving unit 70 generates a driving force and transmits the generated driving force to the shaft-fixing tube body 40, thereby enabling the end effector 30 to rotate relative to the steering unit 20.

The rotation driving unit 70 may include a rotation driving motor 73.

The rotation driving motor 73 is connected to a power source (not shown) to receive a power and generate a rotation driving force. In addition, a control board 73a for sensing a rotation angle of the tube unit 10 and controlling the rotation angle may be electrically connected to the rotation driving motor 73.

The tube unit 10 is connected to the rotation driving motor 73 and receives the rotation driving force generated by the rotation driving motor 73 to rotate, thereby transmitting a rotational force to the steering unit 20. The rotation driving motor 73 may rotate a plate 75 supporting the driving gear 65 as well.

In addition, as shown in FIG. 4, the endoscope apparatus 100 of the present disclosure may further include a base portion 80 that supports the steering driving unit 60 and the rotation driving unit 70 at the base thereof.

The endoscope robot of the present disclosure may allow to observe all directions at various angles without replacing an endoscope in use just with a simple structure, and thus it is possible to allow a user to focus more on the surgical procedure.

In addition, the endoscope robot of the present disclosure is easy to control because its mechanical mechanism is simple and its modeling is simple, and a working area may be advantageously secured due to a small operation volume.

Also, since the endoscope robot of the present disclosure does not need to treat an image to maintain a direction, it is not required to cut the image into a circular shape, and the image may also be used for a 3D image.

Meanwhile, the endoscope robot of the present disclosure may be applied to a single port system into which the endoscope robot may be inserted together with other devices.

The endoscope apparatus 100 of the present disclosure as described above is not limited to the configuration and method of the embodiments described above, but the embodiments may be modified in various ways by combining the embodiments entirely or selectively.

It will be apparent to those skilled in the art that the present disclosure can be embodied in other specific forms without departing from the essential characteristics of the present disclosure. Accordingly, the above detailed description should be considered in all respects as illustrative and not restrictive. The scope of the present disclosure shall be determined by rational interpretation of the appended claims, and all changes within the equivalence scope of the present disclosure shall fall within the scope of the present disclosure.

What is claimed is:

1. An endoscope apparatus, comprising:
    a tube unit coupled to a rotary shaft to which a rotational force is transmitted so as to be rotatable, the tube unit being formed to extend in one direction;
    a steering unit having one end installed at one end of the tube unit to rotate with respect to the tube unit so that a direction thereof facing forward is adjusted, the steering unit rotating together with the tube unit by the rotational force transmitted from the tube unit;
    an end effector installed inside the steering unit to rotate together with the steering unit due to the rotation of the steering unit, the end effector being disposed to face forward; and
    a shaft-fixing tube body installed at the end effector,
    wherein the direction of the steering unit facing forward and a relative rotation of the steering unit with respect to the end effector are adjustable;
    wherein a steering protrusion is protrusively formed on an outer circumference at one end of the steering unit, the steering protrusion extending through a steering hole formed at one end of the tube unit such that the steering unit can rotate relative to the tube unit about the steering protrusion; and
    wherein a first wire hole is formed in a first side of the steering unit and a second wire hole is formed in a second side of the steering unit with respective wires installed therein, the wire holes formed at both sides with the steering protrusion being interposed therebetween, and the direction of the steering unit facing forward is adjusted by changing a tension of the wires respectively installed in the wire holes.

2. The endoscope apparatus according to claim 1, wherein a guide protrusion is protrusively formed on an outer circumference of the end effector so that the end effector is guided to rotate by the rotation of the steering unit, and a rotation guide is formed at the steering unit along a rotation direction of the steering unit to accommodate the guide protrusion.

3. The endoscope apparatus according to claim 1, wherein a connection member is installed between the end effector and the shaft-fixing tube body to connect the end effector and the shaft-fixing tube body,
    wherein the connection member includes a first protrusion protruding to connect the end effector relatively rotatably and a second protrusion protruding to connect the shaft-fixing tube body relatively rotatably, and
    wherein a hole is formed in the end effector so that the first protrusion is rotatably inserted therein, and a hole is formed in the shaft-fixing tube body so that the second protrusion is rotatably inserted therein.

4. The endoscope apparatus according to claim 3, wherein a rotation cut portion is formed at an outer circumference of the shaft-fixing tube body adjacent to the hole into which the second protrusion is rotatably inserted, to have a space in which the end effector is rotatable.

5. The endoscope apparatus according to claim 1, wherein a steering cut portion is formed at an outer circumference of the tube unit adjacent to the steering hole to have a space in which the steering unit is rotatable.

6. The endoscope apparatus according to claim 1, further comprising:
    a steering driving unit configured to generate a driving force and transmit the generated driving force to the steering unit so that the steering unit is rotatable with respect to the tube unit,
    wherein the steering driving unit includes:
        a steering driving motor connected to a power source to generate a rotation driving force by receiving a power therefrom; and
        a driving gear connected to the steering driving motor to receive a rotation driving force generated by the steering driving motor and transmit a driving force to enable the wire to be wound or unwound; and
    wherein the wires are connected to the driving gear and installed at respective wire holes of the steering unit.

7. The endoscope apparatus according to claim 1, further comprising:
    a rotation driving unit configured to generate a driving force and transmit the generated driving force to the shaft-fixing tube body so that the steering unit is rotatable with respect to the end effector, wherein the rotation driving unit includes a rotation driving motor connected a power source to generate a rotation driving force by receiving a power therefrom, and wherein the tube unit is connected to the rotation driving motor to rotate by receiving the rotation driving force generated by the rotation driving motor, and the tube unit allows the rotational force to be transmitted to the steering unit.

* * * * *